United States Patent [19]
Leitao et al.

[11] Patent Number: 6,143,948
[45] Date of Patent: *Nov. 7, 2000

[54] DEVICE FOR INCORPORATION AND RELEASE OF BIOLOGICALLY ACTIVE AGENTS

[75] Inventors: Eugenia Ribeiro de Sousa Fidalgo Leitao, Tytherington, United Kingdom; Joost Dick De Bruijn, The Hague, Netherlands; Hai-Bo Wen, Bilthoven, Netherlands; Klaas De Groot, Heemstede, Netherlands

[73] Assignee: IsoTis B.V., Bilthoven, Netherlands

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/901,294

[22] Filed: Jul. 3, 1997

Related U.S. Application Data

[63] Continuation-in-part of application No. 08/855,833, May 12, 1997, abandoned.

[30] Foreign Application Priority Data

May 10, 1996 [EP] European Pat. Off. .............. 96201293

[51] Int. Cl.⁷ ...................................... A61F 2/02
[52] U.S. Cl. ............................ 623/11; 623/16; 433/201.1
[58] Field of Search ................................. 623/11, 16, 18, 623/20, 21, 22, 23; 433/199.1, 200.1, 201.1

[56] References Cited

U.S. PATENT DOCUMENTS

| | | | |
|---|---|---|---|
| 3,984,914 | 10/1976 | Schwartz | 32/10 |
| 4,145,764 | 3/1979 | Suzuki et al. | 3/1.9 |
| 4,330,891 | 5/1982 | Brånemark et al. | 3/1 |
| 4,538,306 | 9/1985 | Dorre et al. | 623/20 |
| 4,636,526 | 1/1987 | Dorman et al. | 521/61 |
| 4,687,487 | 8/1987 | Hintermann | 623/18 |
| 4,746,532 | 5/1988 | Suzuki et al. | 427/2 |
| 4,818,559 | 4/1989 | Hama et al. | 427/2 |
| 4,846,837 | 7/1989 | Kurze et al. | 623/16 |
| 4,847,163 | 7/1989 | Shimamune et al. | 428/469 |
| 4,863,474 | 9/1989 | Brown et al. | 623/16 |
| 4,879,136 | 11/1989 | Pölz | 427/2 |
| 4,880,610 | 11/1989 | Constantz | 423/305 |
| 4,911,953 | 3/1990 | Hosonuma et al. | 427/224 |
| 5,030,474 | 7/1991 | Saita et al. | 427/2 |
| 5,071,434 | 12/1991 | Tsuzuki et al. | 623/16 |
| 5,071,436 | 12/1991 | Huc et al. | 623/16 |
| 5,128,169 | 7/1992 | Saita et al. | 427/2 |
| 5,141,576 | 8/1992 | Shimamune et al. | 427/2 |
| 5,180,426 | 1/1993 | Sumita | 106/35 |
| 5,205,921 | 4/1993 | Shirkanzadeh | 623/16 |
| 5,219,361 | 6/1993 | von Recum et al. | 623/11 |
| 5,344,457 | 9/1994 | Pilliar et al. . | |
| 5,358,529 | 10/1994 | Davidson | 623/20 |
| 5,456,723 | 10/1995 | Steinemann et al. . | |
| 5,478,237 | 12/1995 | Ishizawa | 433/173 |
| 5,484,286 | 1/1996 | Hansson | 433/201.1 |
| 5,603,338 | 2/1997 | Beaty | 128/898 |
| 5,730,598 | 3/1998 | Story et al. | 433/201.1 |
| 5,766,669 | 6/1998 | Pugh et al. | 427/2.27 |
| 5,947,893 | 9/1999 | Agrawal | 623/16 |

FOREIGN PATENT DOCUMENTS

| | | |
|---|---|---|
| 0450939 | 10/1991 | European Pat. Off. . |
| 2045083 | 10/1980 | United Kingdom . |
| WO 9513101 | 5/1995 | WIPO . |
| WO 9513102 | 5/1995 | WIPO . |
| WO 96/39202 | 12/1996 | WIPO . |

Primary Examiner—Paul B. Prebilic
Attorney, Agent, or Firm—Banner & Witcoff, Ltd.

[57] ABSTRACT

The invention provides an implantable device coated with a layer of calcium phosphate and optionally one or more biologically active substances such as growth factors, lipids, (lipo)polysaccharides, hormones, proteins, antibiotics or cytostatics. The device can be obtained by a nanotechnology process comprising subjecting a substrate to a surface treatment until a surface roughness with an average peak distance (Ra value) between 10 and 1,000 nm and subjecting the roughened surface to precipitation of calcium phosphate from a solution containing calcium and phosphate ions with optional coprecipitation of the biologically active substance.

10 Claims, 15 Drawing Sheets

DEVICE FOR INCORPORATION AND RELEASE OF BIOLOGICALLY ACTIVE AGENTS

This application is a continuation-in-part application of Ser. No. 08/855,833 filed May 12, 1997 and now abandoned.

BACKGROUND OF THE INVENTION

The present invention relates to an implantable device with a specific surface roughness that facilitates in vitro formation of a solution mediated coating, including calcium phosphate coatings, in which biologically active substances can be coprecipitated. The present invention further relates to a process of producing such a device and to the biomedical use of such a device.

U.S. Pat. No. 5,456,723 discloses an implant having a porous metallic surface which has been treated by sandblasting and reductive acid etching resulting in a surface microroughness having a maximum peak-to-valley height of about 20 to 30 μm and a roughness spacing of from 0.5 to 10 μm, preferably of about 1–5 μm. The extremely sharp, comb-like structure is necessary in order to achieve sufficient adhesion between the implant and the coating material (hydroxyapatite) formed on it by anchoring the hydroxyapatite in the implant.

A drawback of most hydroxyapatite-coated implants is that the anchoring of hydroxyapatite onto the implant requires high processing temperatures, which limit the choice of substrate materials and result in higher processing costs. The previously preferred technique for coating implant materials with hydroxyapatite is plasma deposition (for a review, see P. Serekian, in *Hydroxylapatite Coatings in Orthopaedic Surgery*, Ed. Geesink and Manley, Raven Press N.Y., 1993, p. 81–87). Another disadvantage of the plasma deposition technique, in addition to the high temperatures involved, resides in the relatively large particle size, in the order of 30–70 μm.

An aim of the present invention is to provide a coated implantable device that can be used in a wide variety of biomedical applications (surgery, bone-replacement, prosthodontics etc.). The device should give rise to effective bone formation and simultaneously result in a desired biological effect, such as assisting bone formation, preventing infection or rejection during or after implantation, induced by the presence of biologically active substances, such as proteins, growth-factors, lipids, (lipo)polysaccharides, cytostatic agents, hormones, antibiotics or other biological agents. In case a degradable coating is produced, degradation of said coating due to solution mediated processes or cell mediated processes should result in a further exposure or release of biologically active agents. The processing of the device and the temperature at which it is produced should not have an adverse effect on the biological activity of said agents.

SUMMARY OF THE INVENTION

The aim is achieved by a shaped article suitable as an implant of a solid, i.e. non-fluid, porous or non-porous material having a surface nano-roughness, giving rise to the formation of a composite coating when placed in certain solutions. Said solutions contain, but are not limited to calcium and phosphate ions, and biologically active agents (e.g. proteins, growth-factors, lipids, (lipo)polysaccharides, cytostatic agents, hormones, antibiotics) and may be saturated or supersaturated, but may also be relatively diluted. The coating can therefore be composed of both an organic phase, such as the biologically active agent and an inorganic (e.g. calcium phosphate) phase. The uniqueness about the present invention is that biologically active agents can be simultaneously co-precipitated during the formation of the solution mediated coating. As a result, a specified area in the coating or the whole thickness of said coating can be loaded with the biologically active agent(s), that expresses its use when exposed or released at the surface. Depending on the time at which the biologically active agent is added to the solution, said agent can be accurately co-precipitated anywhere throughout the thickness of the coating, as the coating formation is a time-dependent process and elimination of said agent from the solution results in the formation of an inorganic coating (i.e. a calcium phosphate coating). Utilizing such a co-precipitation technique where biologically active agents can either or not be co-precipitated at different time points and with different concentrations, can result in a wide variety of coatings, from relatively simple coatings in which a homogenous concentration of a co-precipitated biologically active agent is present, to a very complex coating containing, at different levels, different concentrations of different biologically active agents.

The surface roughness is an important factor of the device according to the invention. The surface roughness is defined herein by the average peak distance, i.e the average spacing between protrusions on the surface (Ra value). This average peak distance can be determined e.g. by means of Scanning Electron Microscopy (SEM). In general, the average peak distance may be 1,000 nm or less, down to 10 nm. The most suitable roughness depends on the nature of the material of the article. For articles made of titanium, the average peak distance can be e.g. from 10 to 200 nm, for polymeric material, the preferred peak distance is from 20 to 500 nm, whereas for stainless steel the peak distance is advantageously between 50 and 1,000 nm. In general, the preferred average peak distance range is between 2 and 500 nm.

The depth of the surface roughness of the article is less critical than the peak distance. However, a minimum depth is desirable, in particular a peak height—with respect to the deepest sites on the surface—of at least 20 nm, up to about 2,000 nm. The preferred average depth is of the same order of magnitude as the average peak distance, and is in particular from 50 nm to 1,000 nm. The average depth can also be determined by means of Scanning Electron Microscopy.

The substrate of the implant article can be of various materials. These include metals, in particular biocompatible metals such as titanium, tantalum, niobium, zirconium and alloys thereof, as well as stainless steel. Another useful class of biocompatible materials comprises organic natural and synthetic polymers such as polyethylene, polypropylene, polytetrafluoroethylene (Teflon®), which may also be biodegradable polymers such as polyglycolic acid, polylactic acid or certain polysaccharides. Ceramic materials such as calcium phosphate, alumina or bioglass, as well as composite materials, can also be used as an implant substrate. The material may be porous or non-porous. Where it is porous, the pores are distinguished from the valleys of the surface roughness by the depth: i.e. the pores have depths substantially greater than 2 μm, and the surface roughness may be superimposed on the pore walls.

The substrate having the desired surface roughness can efficiently be coated in vitro with a layer of a calcium phosphate and one or more biologically active agents. The composite coating can be relatively thin, on the order of from a a e.g. 50 nm to 200 μm, especially from 1 to 50 μm. The calcium phosphate preferably forms small crystals, producing an amorphous-like structure. The calcium phosphate can be any combination of calcium and phosphate ions, optionally together with e.g. hydroxide, chloride, sulphate, nitrate etc. anions or hydrogen, sodium, potassium, magnesium etc. cations. For a faster process, the deposition step can be preceded by a precalcification step using a solution of calcium and phosphate ions, or two solutions containing calcium ions and phosphate ions respectively and applied consecutively. The biologically active agent in the coating includes, but is not limited to, single or combinations of proteins, lipids, (lipo)polysaccharides, growth-factors, cytostatic agents, hormones, and antibiotics. Examples of such agents are bone morphogenetic proteins (BMP's), basic fibroblast growth factor (bFGF), transforming growth factor (TGF-β), osteogenic growth peptide (OGP), etcetera. The molecular weight of said biologically active agents can vary from several tens of Daltons, to thousands of kilo-Daltons.

The calcium coating can be applied from a solution containing calcium and phosphate ions and one or more dissolved biologically active agents. The solution may be saturated or even super-saturated, but it may also be relatively diluted. This is an important advantage of the present invention since it allows the formation of a calcium phosphate coating from practically any solution containing calcium and phosphate ions and the biologically active agent. The pH range of the calcium phosphate containing solution may be between 4 and 10, preferentially between 6 and 8. The loading rate of the coating with the biologically active agent(s) can vary from several promilles to 60 percent (in weight with respect to the coating) and depends on the concentration in which it expresses its biological activity. This can be established by varying the concentration of the biologically active agent in the solution. The composite coating can be produced to degrade due to solution mediated or cell mediated processes, or can be prepared as a stable coating that shows little or no degradation.

The implantable device with the calcium phosphate and biologically active agent composite coating can give rise to the acceleration, enhancement or induction of bone formation when implanted when the biologically active agent is composed of an osteoinductive protein, or growth factors.

The invention also provides a process of producing a device as described above, comprising subjecting a solid material to a surface treatment until a surface roughness with the required average peak distance (Ra value) is obtained, and subsequently coating the device with calcium phosphate, optionally together with a biologically active substance.

The surface treatment may e.g. be a sanding or scoring treatment using conventional sandpaper, emery paper or glass paper having an appropriate fineness, e.g. grade 4000, optionally in the presence of water or other fluids. Diamond paste can also be used in the mechanical surface treatment. The surface roughening can further be obtained by powder blasting, using suitable fine powders. The surface roughness may also be obtained by a chemical treatment with a strong, preferably mineral, acid solution, optionally followed by oxidising agents such as hydrogen peroxide, optionally followed by neutralising steps.

The coated implantable devices according to the invention are intended for biomedical use, i.e. as a bone substitute, a joint prosthesis, a dental implant (prosthodontics), a maxillofacial implant, a vertebral surgery aid, a transcutaneous device (stoma and the like) and other medical or cosmetic devices. Such implants can serve as a bone replacement or bone reinforcement, but also as a means of fixing a device to a particular bone.

BRIEF DESCRIPTION OF THE DRAWINGS

Some illustrative embodiments of the invention, and the best mode contemplated of carrying out the invention, are described in detail below with reference to the accompanying drawings in which:—

DETAILED DESCRIPTION OF THE PREFERRED EMBODIMENTS

EXAMPLE 1

Materials and Methods

Ti-6Al-4V and Ti-Al-2.5Fe samples, 9.15 mm and 5 mm in diameter respectively and 1.5 mm thick, were used. They were ground flat in SiC papers, 1200, 4000 grit and diamond polished down to 1 $\mu$m. 316L stainless steel samples, ca. 80 mm$^2$, were also ground in SiC papers, 1200 and 4000 grit. All samples were ultrasonically cleaned in 90% ethanol for 20 minutes followed by a 20-minute double rinse with distilled water and dried under a flow of hot air. The surface roughnesses were measured with a laser profilometer (Perkin Elmer). Table 1 shows the results of the following roughness parameters: $R_a$—arithmetic mean of the roughness height, $R_z$—mean peak-to-valley height and $R_{max}$—maximum roughness depth.

After surface polishing and cleaning, all samples were immersed in HBSS at 37° C. for 14 days in separate polyethylene containers. To allow a constant supply of solution this was changed every 48 hours. Empty polyethylene containers were used as reference. A sample of each retrieved solution was stored in 2 mL Eppendorf™ at 4° C. Ca and P concentrations in these solutions were later determined by atomic absorption spectrometry (Varian SpectAA 300) and spectrophotometry (Vitalab 21, Vitalab Scientific), respectively. All the results are the average of at least three measurements.

All surfaces were observed, before and after immersion, by scanning electron microscopy (Philips SEM 525M) and analysed by XRMA (Voyager XRMA system, NORAN Instruments). XRD (Philips Thin-film XRD) was used to determine the structure of the precipitate layer, and AFM was used to observe its morphology on polished titanium alloys.

Results and discussion

Figure 1:
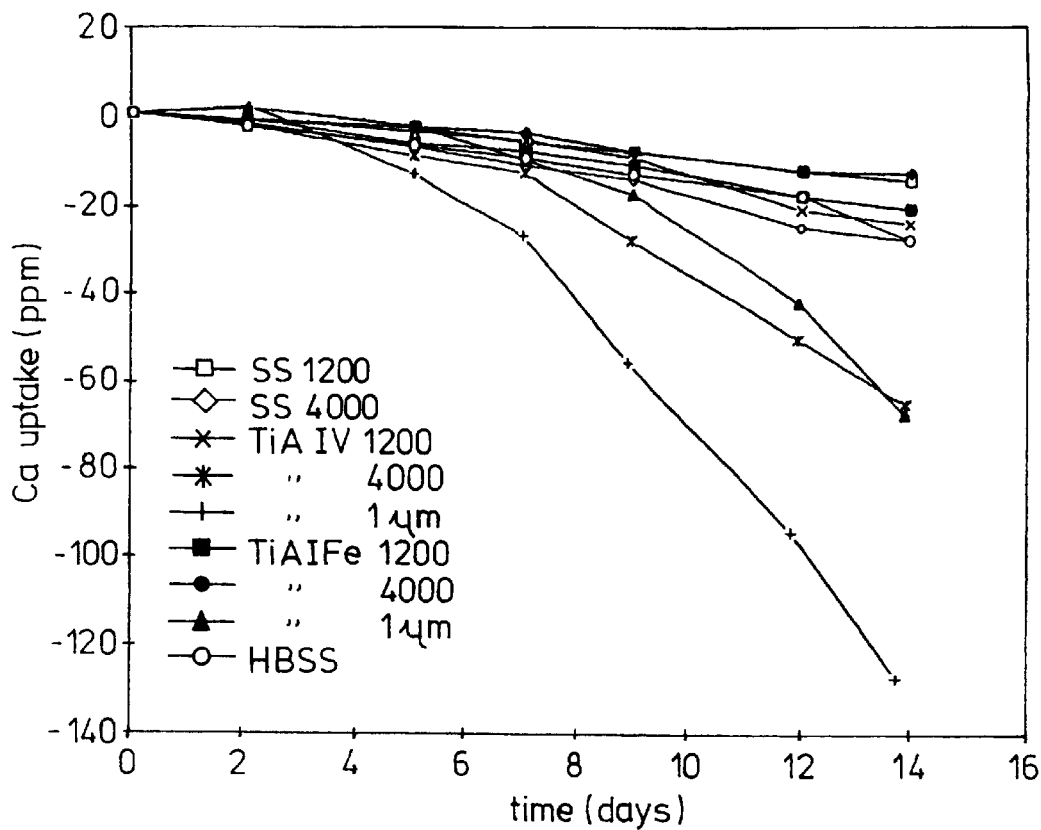
FIG. 1—Ca concentration as a function of time

FIG. 1 shows the Ca concentrations as a function of time. In the solutions that were in contact with the alloys, a monotonic decrease of the concentrations of Ca was detected. The same phenomenon was also observed for the reference HBSS. Until day 5 all curves have similar forms but after day 5 a higher decrease for the Ti-6Al-4V 1 $\mu$m samples is apparent which reaches 123±1.5 ppm. For both Ti-6Al-4V 4000 and Ti-Al-2.5Fe 1 $\mu$m samples the Ca concentration decreased more rapidly after day 7 attaining similar final Ca uptake concentrations, 61±2.3 and 63±1.5 ppm, respectively. All other surfaces exhibited Ca uptake values between 5 and 20 ppm.

Figure 2:
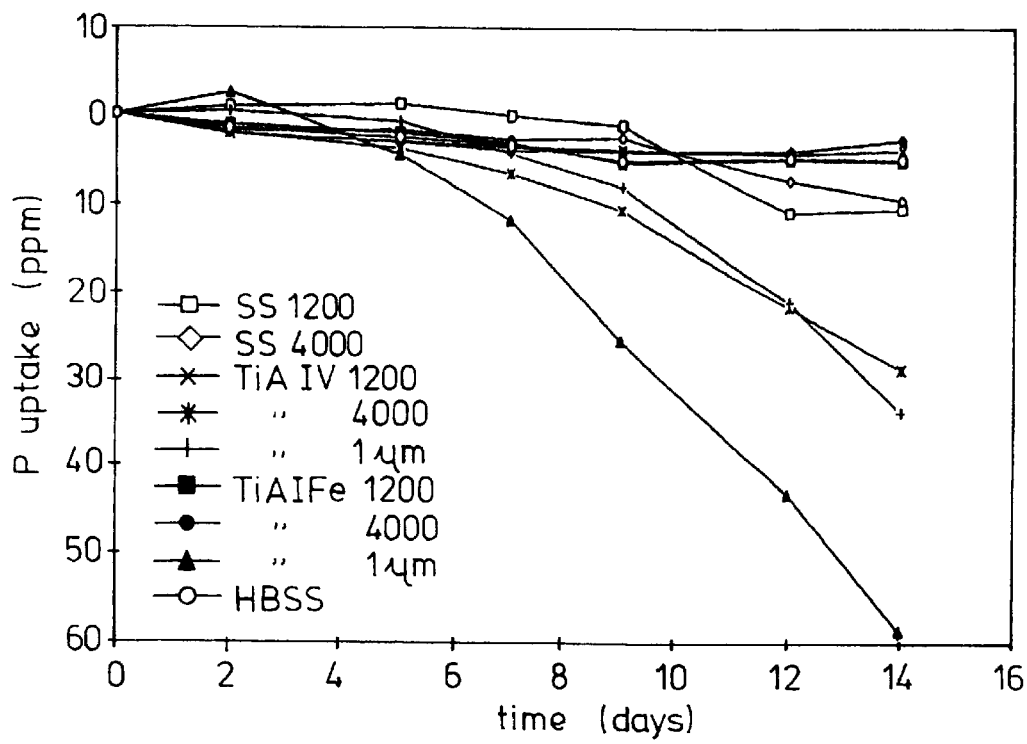
FIG. 2—P concentration as a function of time
Figure 3A:
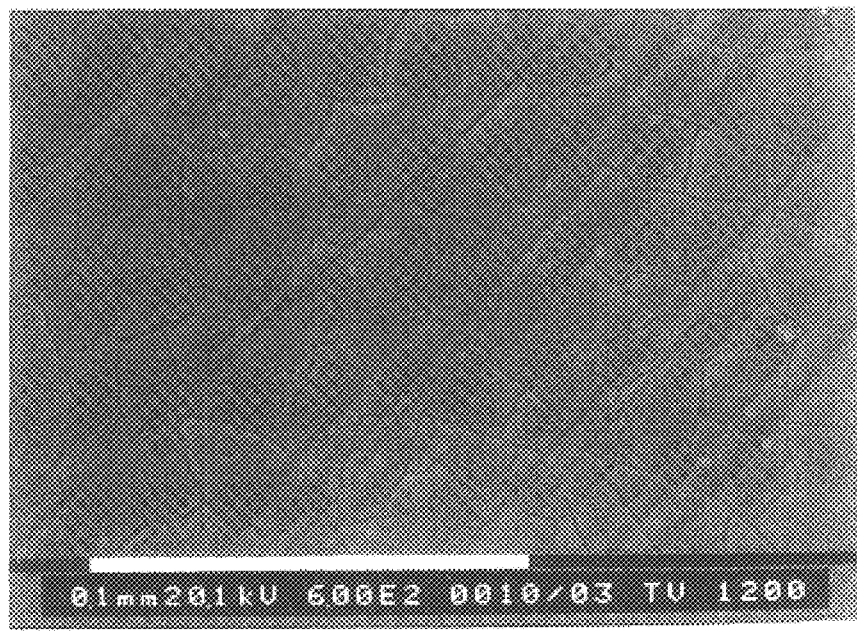
FIG. 3—SEM photomicrographs of the metal surfaces after immersion in HBSS, FIG. 3A Ti-6Al-4V 1200.
FIG. 3B: Ti-6Al-4V 4000.
FIG. 3C: Ti-6Al-4V 1 μm.
FIG 3D: Ti-Al-2.5Fe 1 μm.
FIG. 3E: Ti-Al-2.5Fe 4000.
FIG. 3F—stainless steel 1200
Figure 3B:
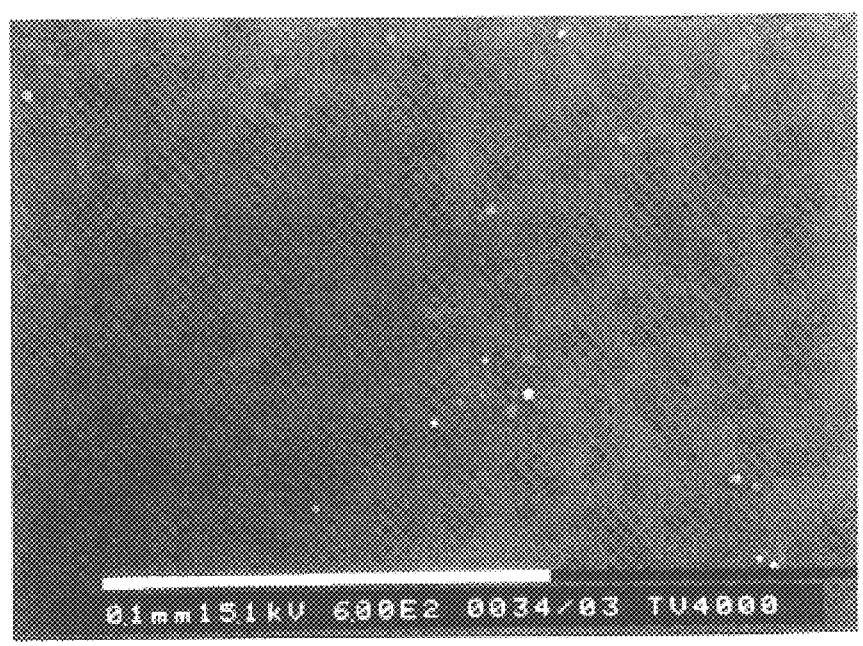
Figure 3C:
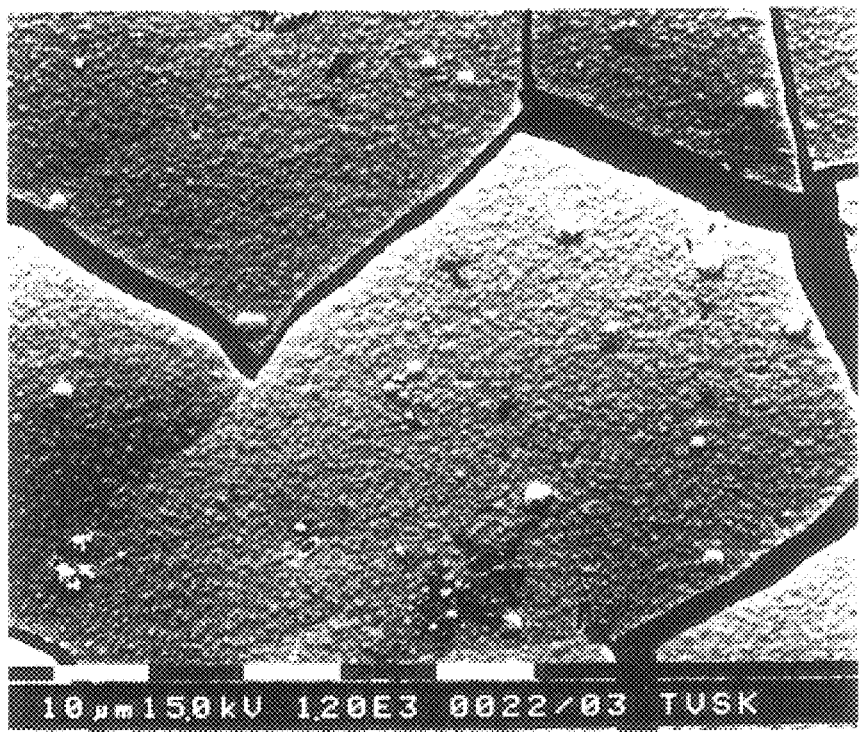
Figure 3D:
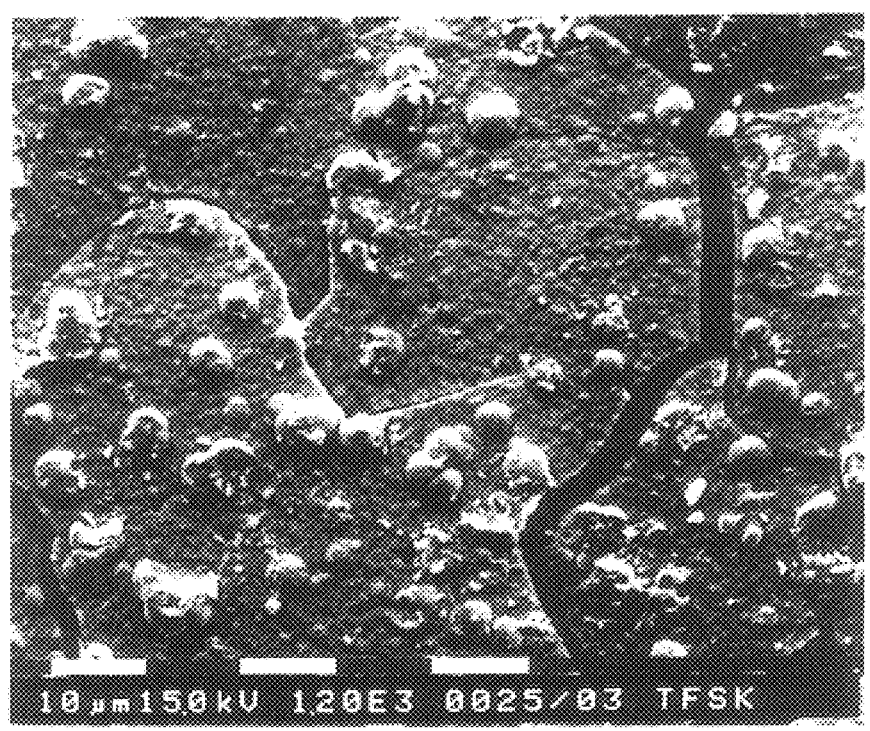
Figure 3E:
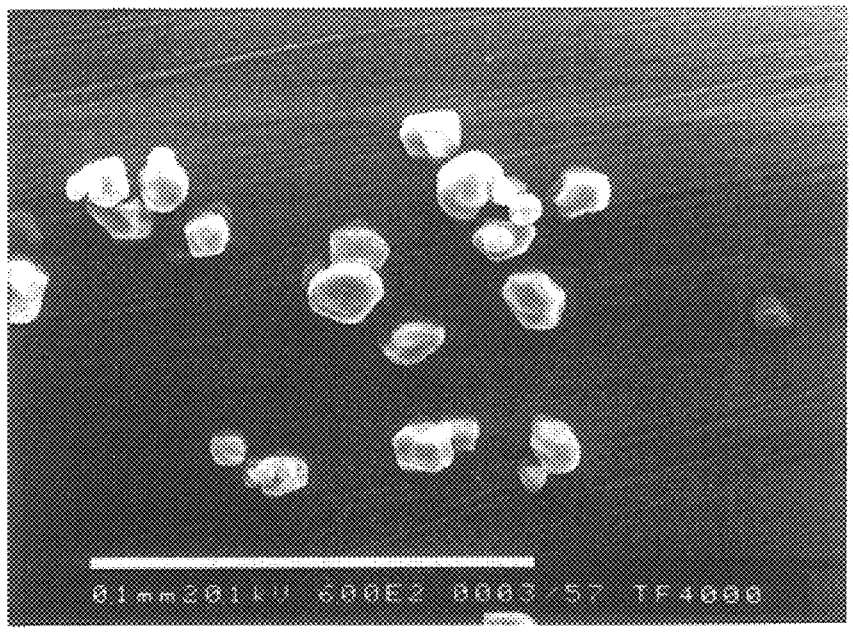
Figure 3F:
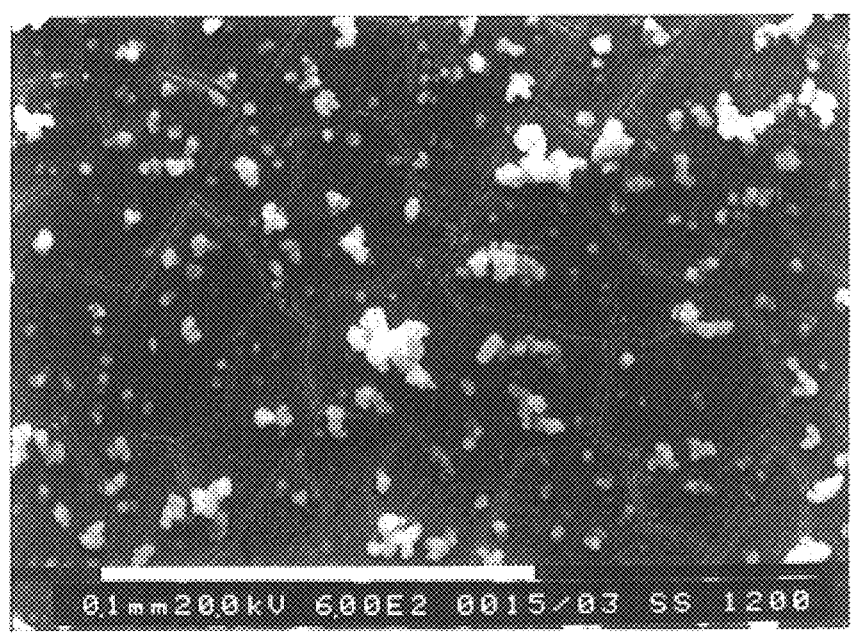

FIG. 2 shows the P concentration as a function of time. The P uptake curves, like the Ca determinations, also showed a decrease as a function of time. The Ti-6Al-4V 4000 and 1 $\mu$m and the Ti-Al-2.5Fe 1 $\mu$m showed the highest P uptake; 29±2.1, 34±1.5 and 58.5±2.2 ppm, respectively. These findings suggest that a Ca and P rich precipitate is formed on all the surfaces from the HBSS. In fact, it was possible to see a white film deposited on the polyethylene that contacted the HBSS. Ti-Al-2.5Fe 4000 and 1200 showed the lowest Ca and P uptake. The decrease in both Ca and P was attributed to the growth of precipitate nuclei on the surfaces from the HBSS solution. Similar behaviour was found by Li et al. [4] after immersion of silica-gel and gel-derived titania in a Simulated Body Fluid; Radin et al. [2] also reported a decrease in Ca and P concentration in Simulated Physiological Solution after the immersion of ceramic particles.

FIG. 3 shows SEM photomicrographs of the metal surfaces after immersion in HBSS. Comparing the photographs on FIG. 3 it can be seen that the precipitate layer has a plate morphology on which "globules" and/or crystals grow. XRMA revealed a higher quantity of Ca and P on these particles than in the plate precipitate. It was possible to observe that the plates fractured on some of the surfaces, namely Ti-6Al-4V 1200 and 1 $\mu$m, Ti-Al-2.5Fe 1 $\mu$m and stainless steel 1200. The orientation of the fractures does not seem to depend on the orientation of the grinding flaws as it is possible to observe a random cracking of the plates. The precipitate formed on Ti-6Al-4V 4000 shows a continuous texture at the same magnification as the other observations. It was only possible to detect fractures on these surfaces, on the Ca and P rich layer, at magnifications higher than 2400×.

Li et al. [4] performed a series of experiments in which silica-gel was immersed in SBF. They suggest that the regulation of apatite growth is related to the Ca/P molar ratio of the fluids. Fugishiro et al. [1] obtained different HA morphologies by immersing Fe and Ti in $Ca(EDTA)^{2-}$—$NaH_2PO_4$ solution. Various concentrations of $Ca(EDTA)^{2-}$ had a direct effect on the morphology of the hydroxyapatite film.

The SEM observations suggest that the morphology of the precipitate layer seems to be dependent both on material and surface finishing as the immersion fluid was the same in all experiments.

Figure 4:
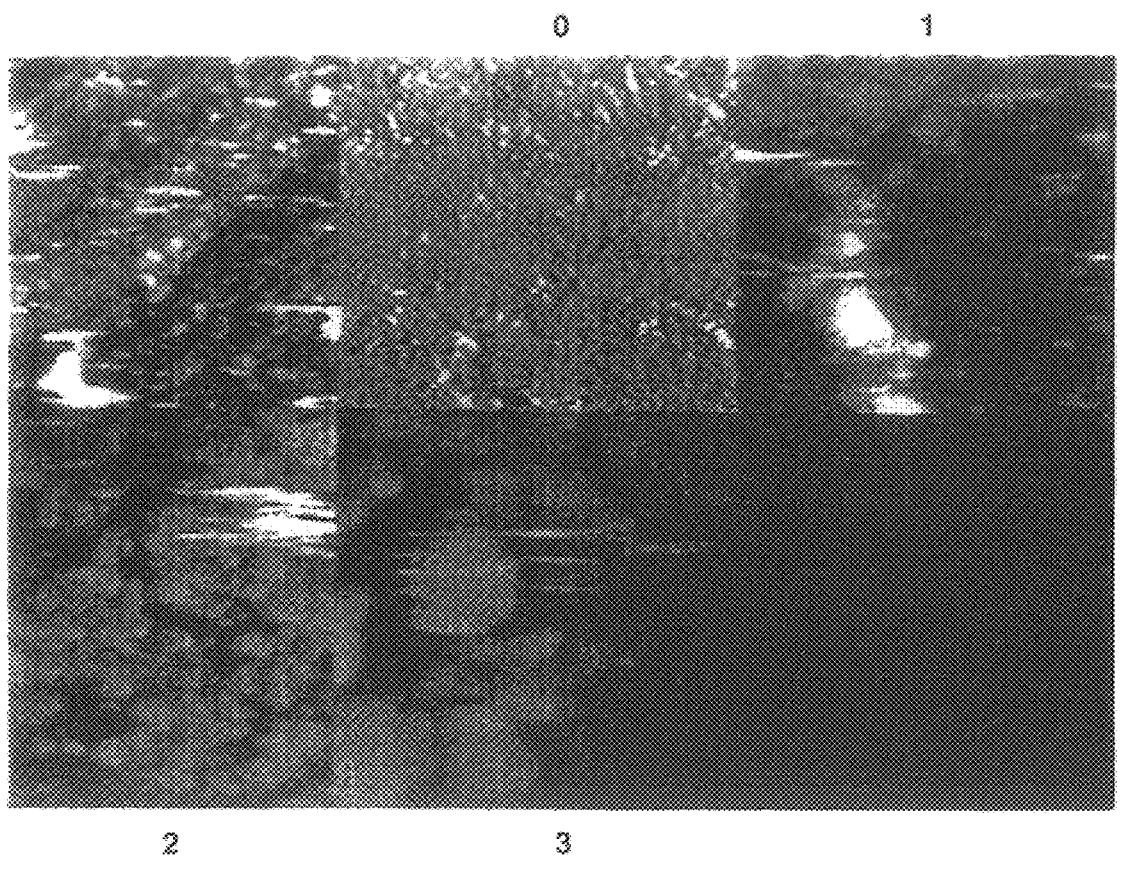
FIG. 4—AFM photomicrograph of a Ti-Al-2.5Fe 1 μm sample after immersion in HBSS. Increasing magnification from field 0 to 3. Scanning length from field 3: 1.5 μm.

FIG. 4 shows an AFM photomicrograph from a Ti-Al-2.5Fe 1 $\mu$m sample. It is apparent that the calcium phosphate rich coating is constituted by the agglomeration of spherical particles. Similar results were obtained for the Ti-6Al-4V 1 $\mu$m surfaces. It seems that the formation of the coating starts with heterogeneous precipitation of nuclei which gather with time until all the surface is covered.

It was noticeable that the Ti-Al-2.5Fe alloy surfaces 4000 and 1200 did not exhibit plate precipitates. It was only possible to observe small scattered deposits which had a similar morphology to crystals. XRMA acquisition on the flat-ground surfaces showed the presence of no Ca or P. The same acquisition on the crystals showed the presence of the alloy elements, Ca and P, associated with Si. Si seems to act as a nucleus for the precipitation and growth of the crystals. This impurity is probably due to the SiC emery paper used during the surface preparation. Either the degreasing and cleaning of the surface was not sufficient, on these surfaces, to remove the SiC or some SiC particles might be anchored in the alloy's surface as Ti-Al-2.5Fe is a softer material than the other alloys.

Figure 5:
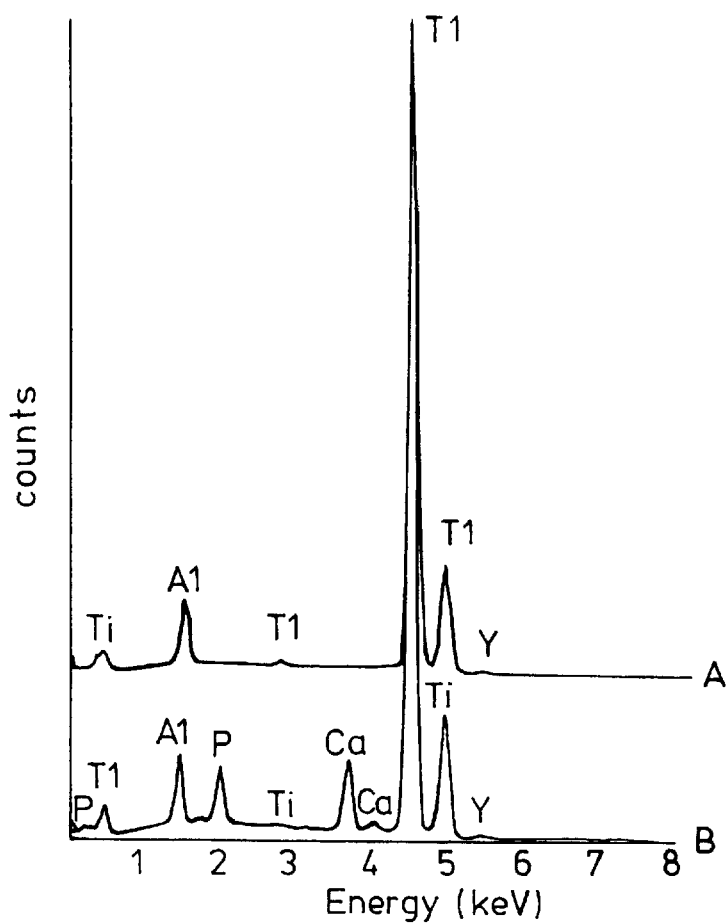
FIG. 5—XRMA spectra acquired on a Ti-6Al-4V 4000 sample before (A) and after immersion (B) in HBSS.

FIG. 5 exhibits XRMA spectra acquired in a Ti-6Al-4V 4000 sample before and after immersion in HBSS. One can observe the presence of the alloy elements as well as very well defined Ca and P peaks on the after-immersion spectra. The calculated Ca/P ratio is 1.56±0.03 which indicates that the precipitate probably consists mainly of tricalcium phosphate.

Figure 6:
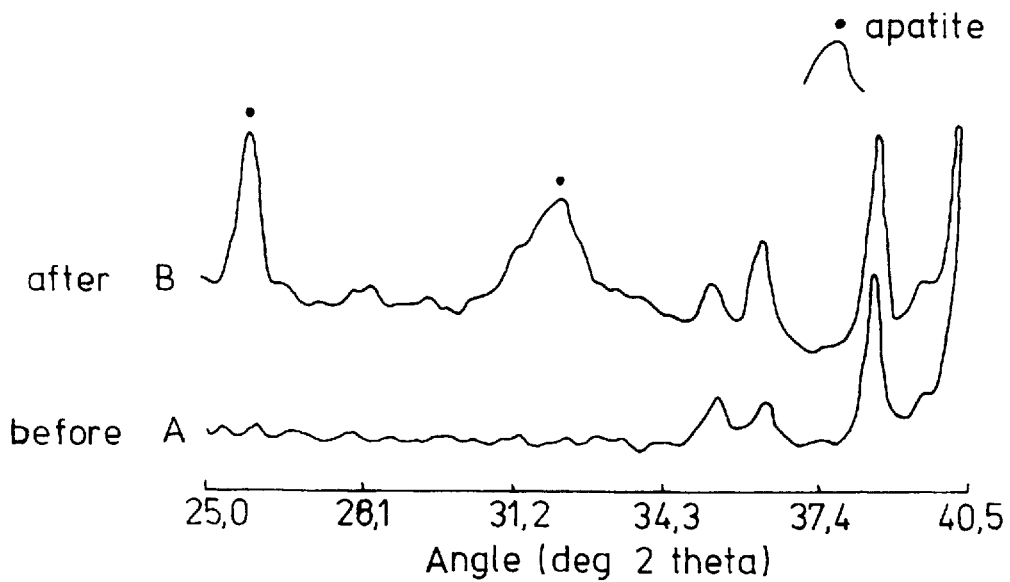
FIG. 6—XRD spectra acquired on a non-immersed (A) and immersed (B) Ti-6Al-4V 1 μm surface FIG. 7. Surface chemical composition (in atomic percent) of the "as received" coating.

FIG. 6 shows XRD spectra acquired on non-immersed (A) and immersed (B) Ti-6Al-4V 1 $\mu$m surfaces. On the immersed samples one can observe the appearance of a well defined [002] peak and a broader peak which seems to be constituted by the junction of peaks [211] and [112] indicating the amorphous characteristics of the calcium phosphate. These results suggest that the precipitate layer has an amorphous apatite-like structure. Similar results were obtained for the Ti-Al-2.5Fe 1 $\mu$m samples.

The thickness of this layer was previously determined by SEM observations and is ca. 5 $\mu$m. Li et al. [4] monitored the development of hydroxyapatite deposits on gel-derived titania, as a function of time, after immersion in Simulated Body Fluid. In the initial stages they detected scattered precipitates all over the surface which increased in number and size until, eventually, all the surface was covered by a 10 μm coating. Ducheyne et al. [5] reported the formation of small deposits on titanium discs after 1-day exposure to a Simulated Physiological Solution. Two weeks of differential immersion were needed to produce an apatite layer with a thickness of 1 μm.

Hanawa et al. [3] also reported that apatite is naturally formed on titanium when titanium is immersed in a solution whose pH is similar to that of the bioliquid. They reported a thickness of 7 nm of the apatite film grown on Ti-6Al-4V which makes it impossible for this layer to exhibit any properties of calcium phosphate in this environment.

The present results indicate that a calcium phosphate with an apatite-like structure is naturally formed on the surfaces of polished titanium alloys. The thickness of this layer makes it a suitable surface for bone induction. Thicknesses of at least 1 μm are needed for the calcium phosphate to show its properties and cause bone induction [5].

Conclusions

The morphology of calcium phosphate precipitates depends on the metal substrate and its surface characteristics. It is possible to produce a naturally formed calcium phosphate coating by immersing metals such as titanium alloys and stainless steel in HBSS. Ti-6Al-4V 4000 seems to be the surface that is most favourable to produce a continuous and more adherent apatite-like coating capable of bone induction.

EXAMPLE 2
Determination of calcium phosphate depth distribution on a titanium alloy substrate using x-ray photoelectron spectroscopy This example illustrates the determination of the depth distributions of selected elements in a calcium, phosphorous and oxygen-containing coating on a titanium alloy sample using depth profiling X-ray Photoelectron Spectroscopy (XPS or ESCA).

Materials

The samples were titanium alloy plates that had been surface treated according to the procedure of Example 1 to produce a calcium phosphate coating when immersed in calcification solutions or simulated body fluids. The samples were mounted directly to a standard XPS sample holder using a spring clip arrangement, with no pre-treatment. The outer coating surface was sufficiently electrically conducting that no electrostatic charging problems were encountered during X-ray irradiation or ion beam etching. All analyses were carried out using a Surface Science Instruments (SSI) M-probe operating at a base pressure of $3 \times 10^{-9}$ torr.

Methods

A survey spectrum was recorded from the "as received" surface, to determine the surface composition of the coating and therefore determine the elements to be monitored for the depth profile. The XPS depth profile was obtained by alternating argon ion sputtering (over an area of approx. 2×2 mm) and data acquisition (from an area of approx. 300 μm diameter centred in the etched crater). Elements analysed were carbon, oxygen, calcium, phosphorus, magnesium and titanium. Etch time per step was variable from 15 to 120 seconds per cycle and the etch rate was 3 nm/min using a total sputter time of 4470 seconds.

Results

Figure 7:
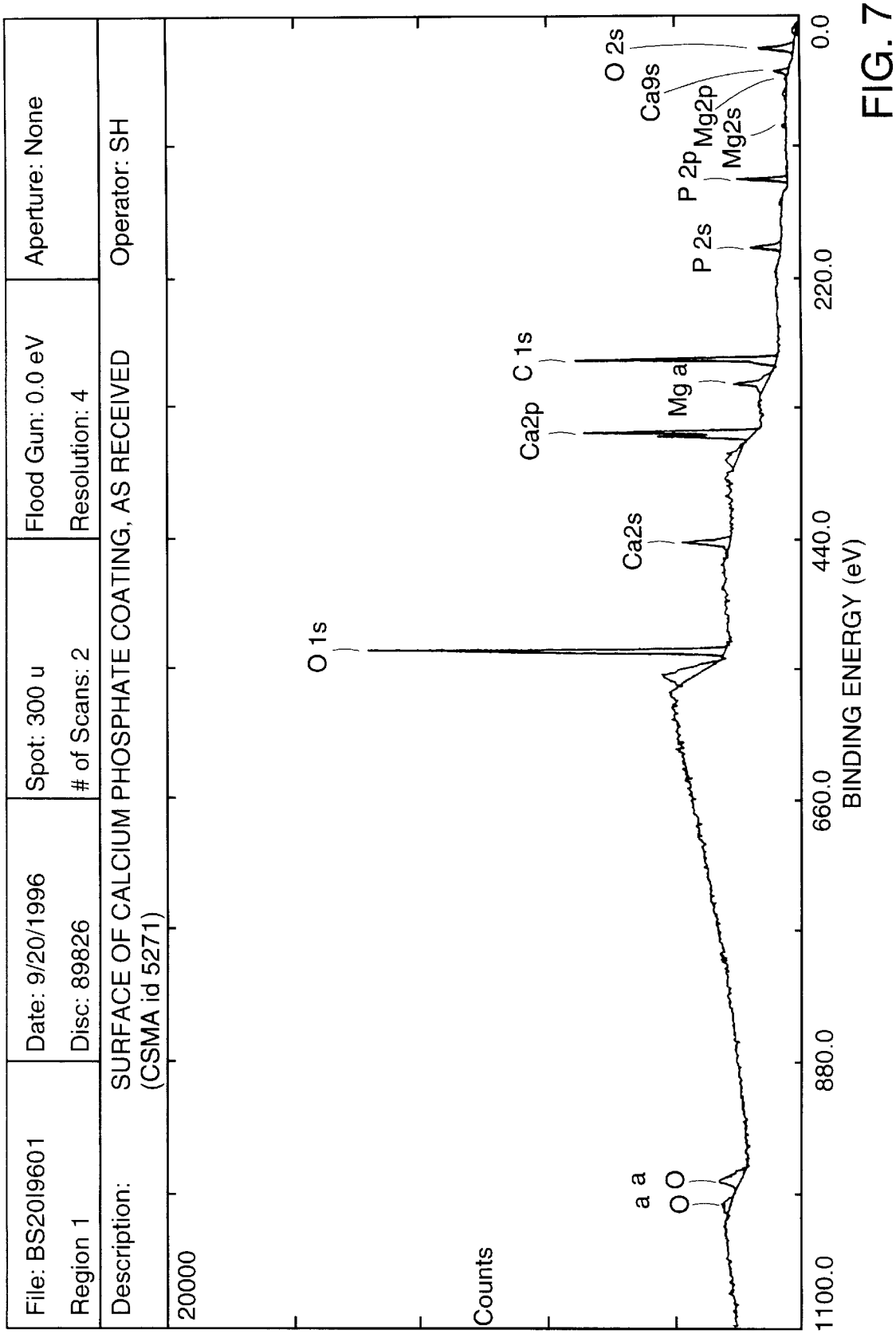
Figure 8:
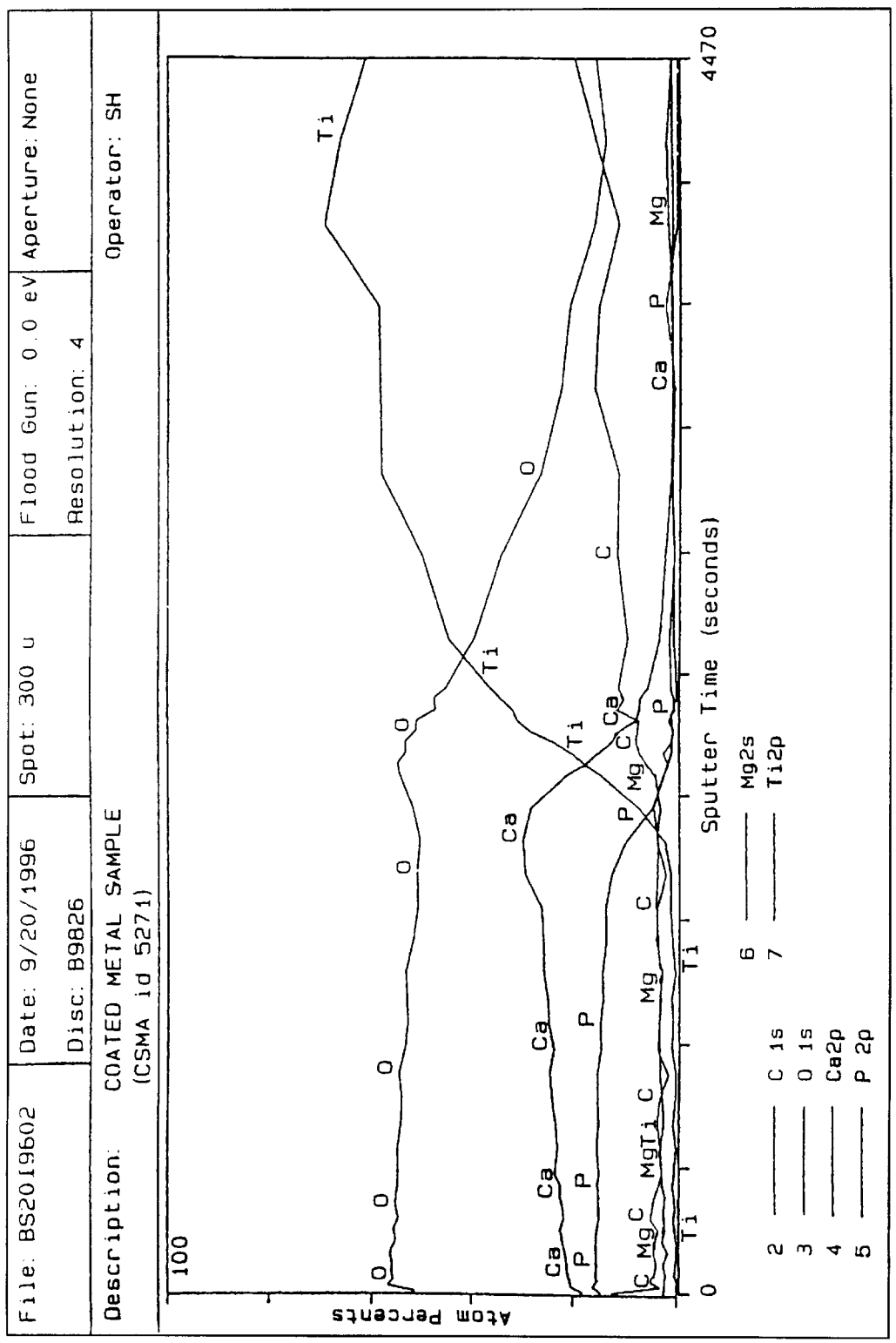
FIG. 8. Depth profile of the coating, from coating to substrate.

The surface chemical composition (in atomic percent) of the "as received" coating was: carbon 44.9%, oxygen 33.8%, calcium 10.5%, phosphorous 8.8%, magnesium 2.0% and titanium 0% (FIG. 7). The depth profile of the coating revealed a gradual transition of calcium and phosphorous from the coating to the substrate, indicating the incorporation of these elements in the surface (oxide layer), and thus a chemical bonding between coating and substrate (FIG. 8). The calcium-oxygen-phosphorous layer (calcium phosphate) is estimated as being approximately 90 nm, assuming a sputter rate of 3 nm per minute as calibrated on a tantalum pentoxide film on tantalum, and that the "interface" is defined as the point where the titanium reaches approx. 50% of its final value. A thin layer of titanium oxide separates the calcium phosphate layer from the titanium alloy substrate. The interface between the calcium phosphate and titanium shows changes in the oxygen, phosphorous, calcium and titanium chemistries. The XPS peak binding energies of calcium and phosphorous decrease at the interface with the titanium where a titanium oxide layer is found. An interphase region is likely to occur at the boundary and oxygen has been depleted from the calcium phosphate to form titanium dioxide at the interface. Metallic titanium is present below the interphase region. Magnesium is detected at 2–4 atomic percent throughout the calcium phosphate layer and increases slightly in concentration with depth towards the interface with the titanium (oxide). Carbon is found in the bulk of the titanium.

Conclusion

The calcium phosphate layer that is formed on the titanium alloy substrate is chemically bound to the substrate via its surface oxide layer.

EXAMPLE 3
Preparation of biomimetic calcium phosphate coatings on metallic implants and co-precipitation of proteins This examples illustrates a new two-step chemical treatment for preparing an implant with a specific surface roughness, resulting in a metallic surface that allows fast precipitation of biomimetic calcium phosphate (Ca-P) coatings from in vitro supersaturated calcification solutions (SCS). The present method has the following advantages over the conventional techniques for the coating application: due to the specific surface roughness, (i) the biomimetic coatings directly induced from SCS are expected to be chemically bound to metallic substrates and to show higher bone-bonding ability, (ii) the coatings can be produced onto complex-shaped and/or macro-porous implants, and (iii) it is a controllable and cost-effective way to acquire Ca-P coatings. To examine the potential of biomimetic calcium phosphate coatings as drug-release carriers, bovine serum albumin (BSA) and Ca-P coatings were co-precipitated on the treated titanium surfaces by immersion in the SCS containing 0.2% wt. BSA. The BSA/Ca-P coatings are expected to serve as a potential drug-release system.

Materials and Methods

A newly developed two-step chemical treatment was performed on the metallic implant materials, i.e. commercially pure titanium (cp.Ti), annealed Ti6Al4V and porous tantalum (Ta), to produce a specific surface roughness. During this treatment, two series of chemical reagents were used for titanium (cp.Ti and Ti6Al4V) and tantalum implant materials, respectively, that resulted in the presence of the specific surface roughness necessary for the preparation of the coating. For the former, the samples were treated with a mixture of HCl and $H_2SO_4$, followed by immersion in a NaOH solution. The porous tantalum samples were treated with a mixture of HCl, $H_2SO_4$ and HF, followed by immersion in $H_2O_2$.

Two kinds of SCSs with different Ca and P concentrations, fast calcification solution (FCS) and commercial Hanks' balanced salt solution (HBSS), were used for preparing biomimetic Ca-P coatings. To promote the Ca-P nucleation on the metallic surfaces, a precalcification (Pre-Ca) procedure was performed on half the treated samples before immersion in the SCS. The Pre-Ca was carried out by incubating the samples in 0.5N $Na_2HPO_4$ overnight and then transferring them into saturated $Ca(OH)_2$ for 5 h. The solution for co-precipitation of BSA and Ca-P coatings was prepared by dissolving 0.2% wt. BSA into FCS. The untreated metals were also immersed as controls. The FCS solution volume used for immersion was 15 ml per $cm^2$ of sample surface area. The samples were immersed in sealed polystyrene vials at 37° C. in a calibrated water-bath. Scanning electron microscopy (SEM) together with energy disperse X-ray (EDX) analyses, X-ray diffraction (XRD) and infrared (IR) spectrophotometry were used to characterize the obtained Ca-P coatings.

Results

The biomimetic Ca-P coatings were fast precipitated on the treated cp.Ti and Ti6Al4V samples by immersion in both FCS and HBSS no matter whether the Pre-Ca procedure was performed or not. But the Pre-Ca treatments could dramatically speed-up the precipitation rate of the Ca-P coatings as listed in table 2.

Figure 9:
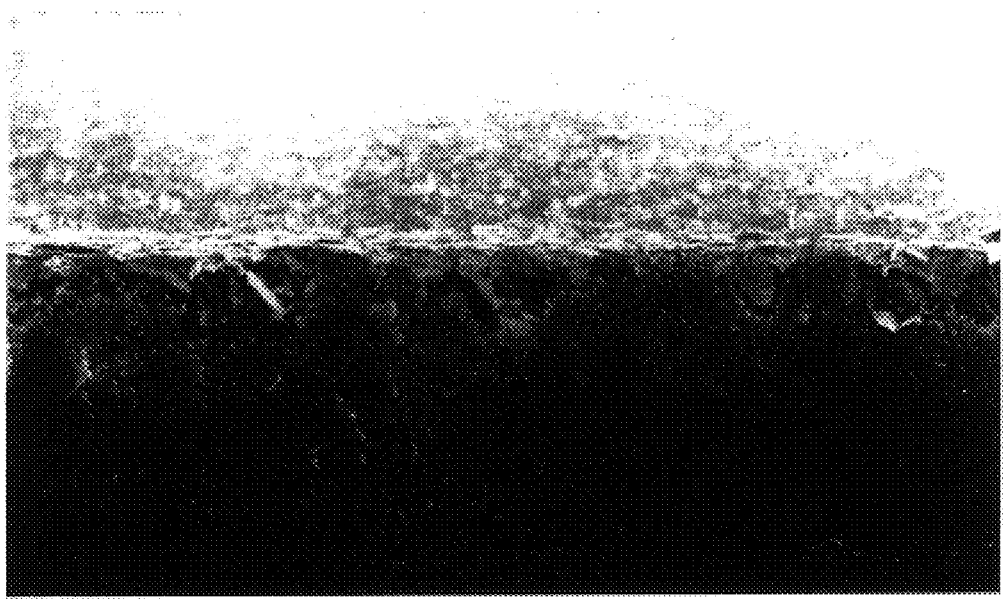
FIG. 9. Scanning electron micrograph of the Ca-P coating (CP) precipitated on cp.Ti (Ti) after 16 hours of immersion in FCS with Pre-Ca.
Figure 12:
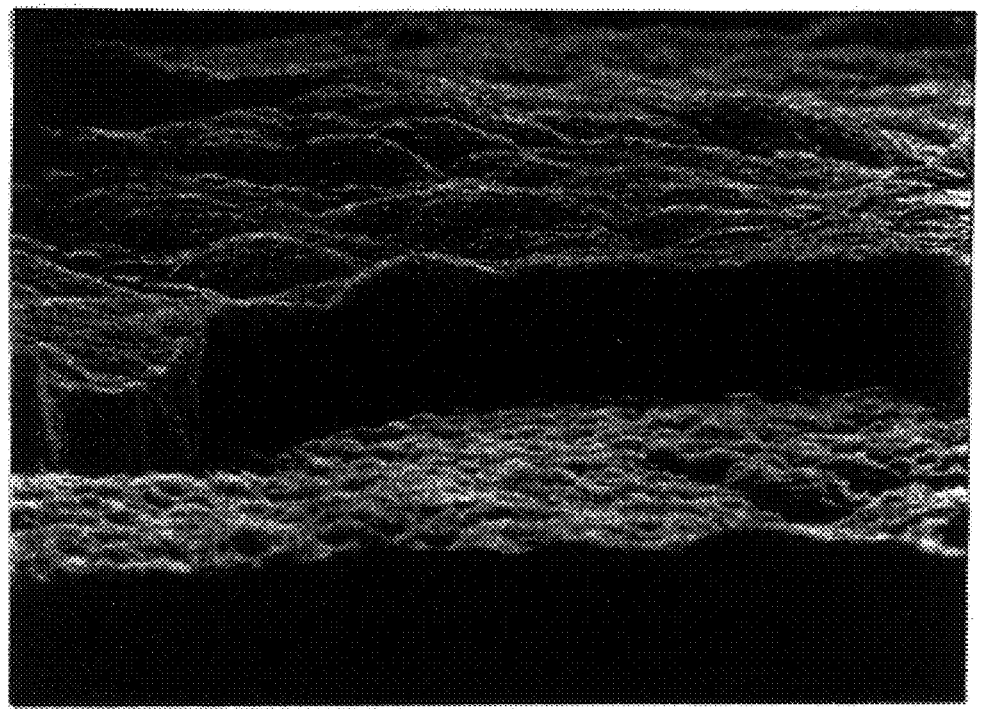
FIG. 12. Scanning electron micrograph of a dense Ca-P coating (CP) precipitated on cp.Ti from HBSS after 1 week of immersion with Pre-Ca. The layer between coating and substrate is the titanium oxide layer (OL), formed as a result of the treatment. Note the surface roughness of the implant on which the calcium phosphate coating has been formed.
Figure 10:
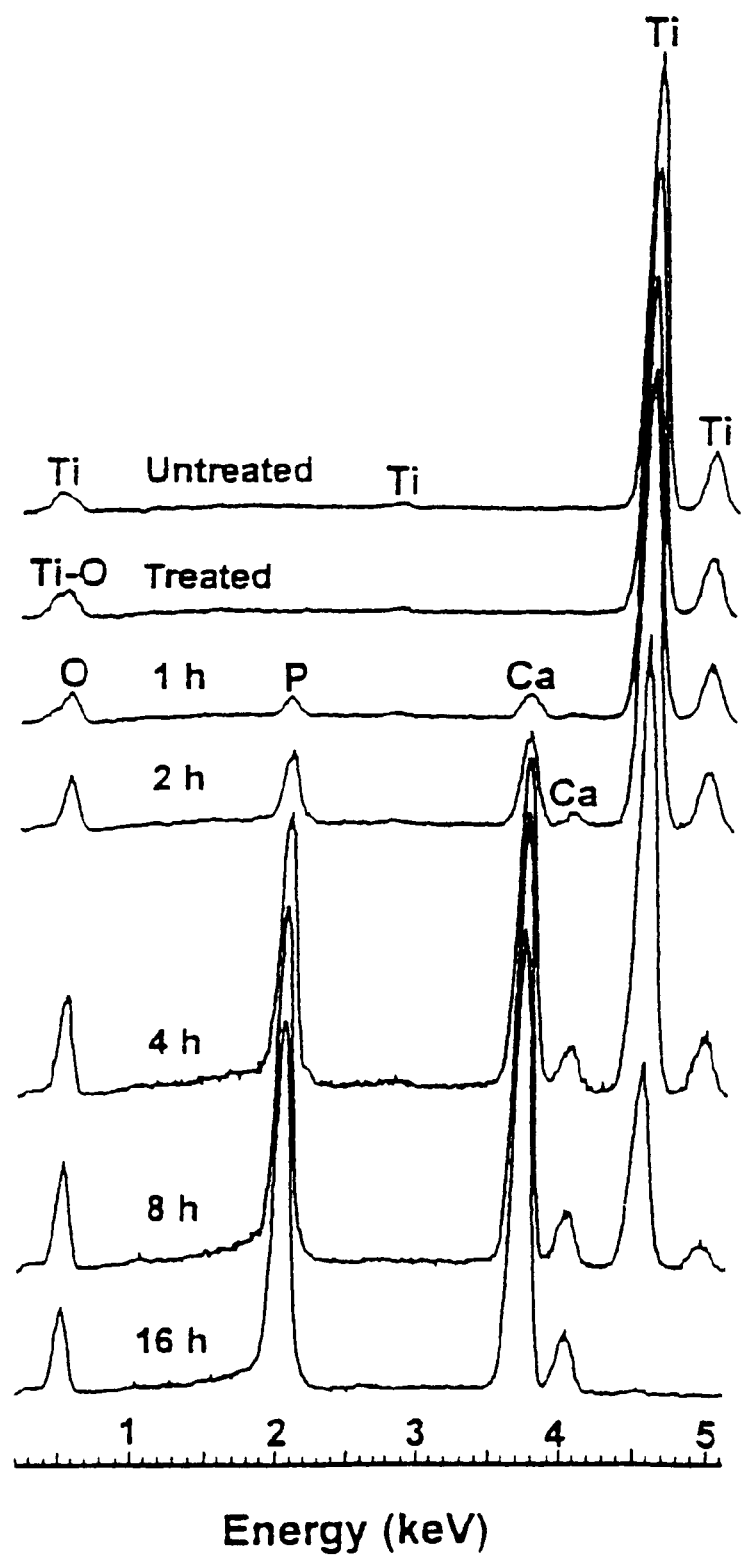
FIG. 10. EDX spectra of the cp.Ti surfaces non-treated, treated and immersed in FCS with Pre-Ca for different hours. The shoulder of O kα peak is clearly seen after the treatment. The Ca and P contents increased with the increase of immersion time.
Figure 11:
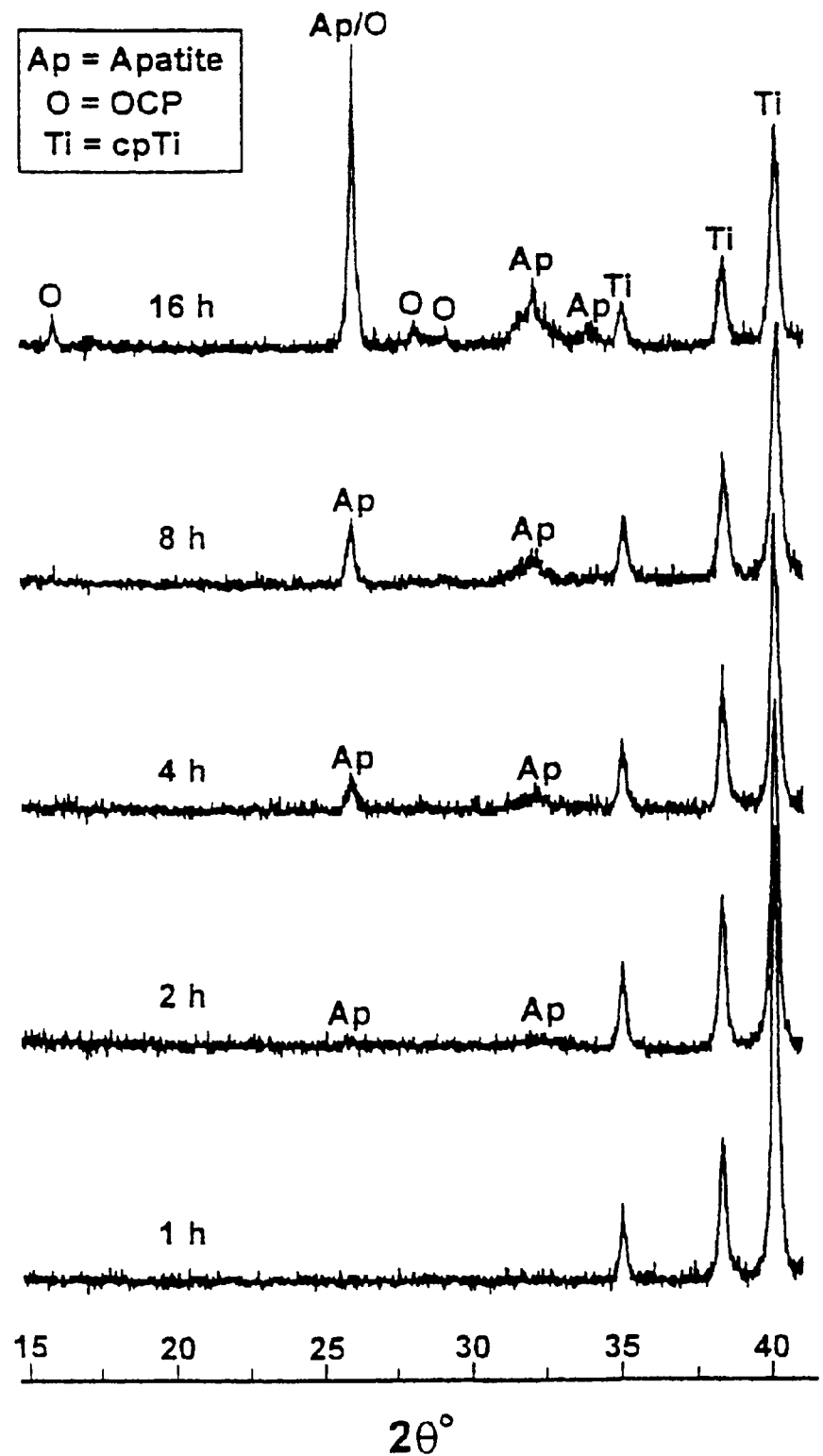
FIG. 11. XRD patterns of the cp.Ti surfaces after different hours of immersion in FCS with Pre-Ca. The counts of apatite peaks get higher with increased immersion times. Octa-calcium phosphate (OCP) starts to be formed at around 8 hours.
Figure 13:
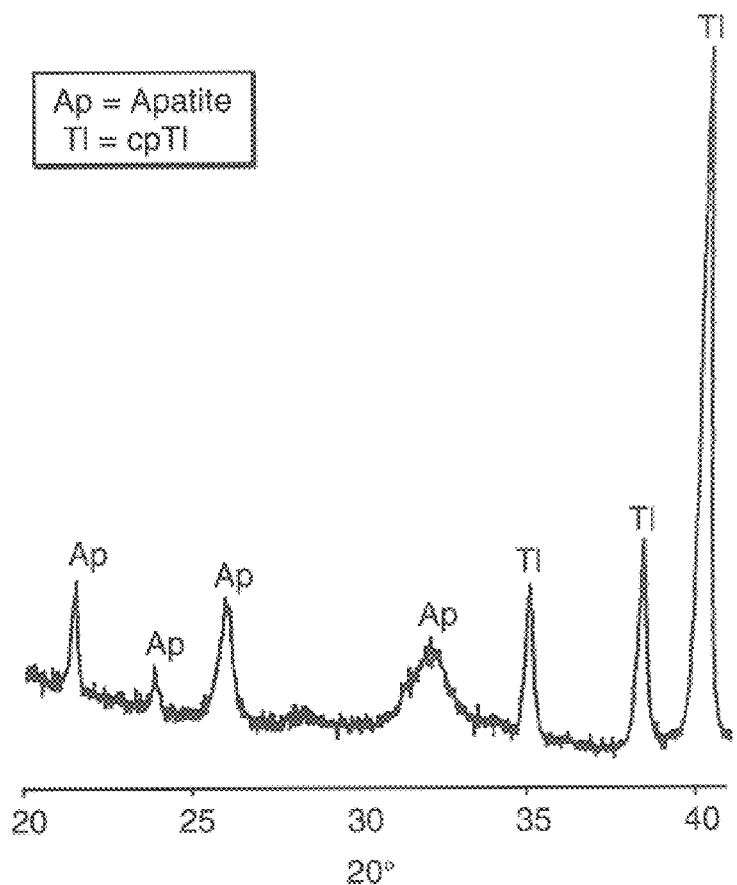
FIG. 13. Thin-film XRD pattern of a dense Ca-P coating deposited by immersion in HBSS with Pre-Ca for 1 week.
Figure 14:
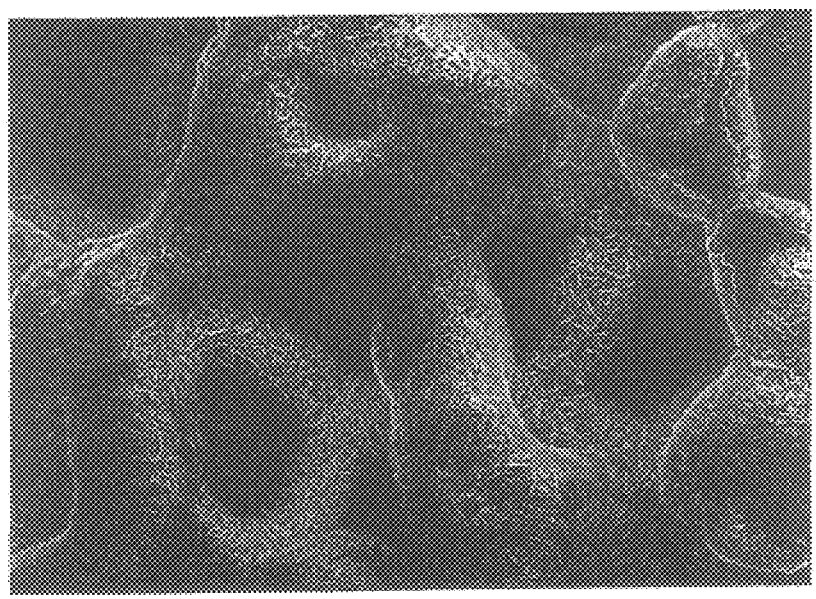
FIG. 14. Scanning electron micrograph of porous tantalum (Ta) after 2 days immersion in FCS with Pre-Ca. The coating is formed throughout the porous material.
Figure 15:
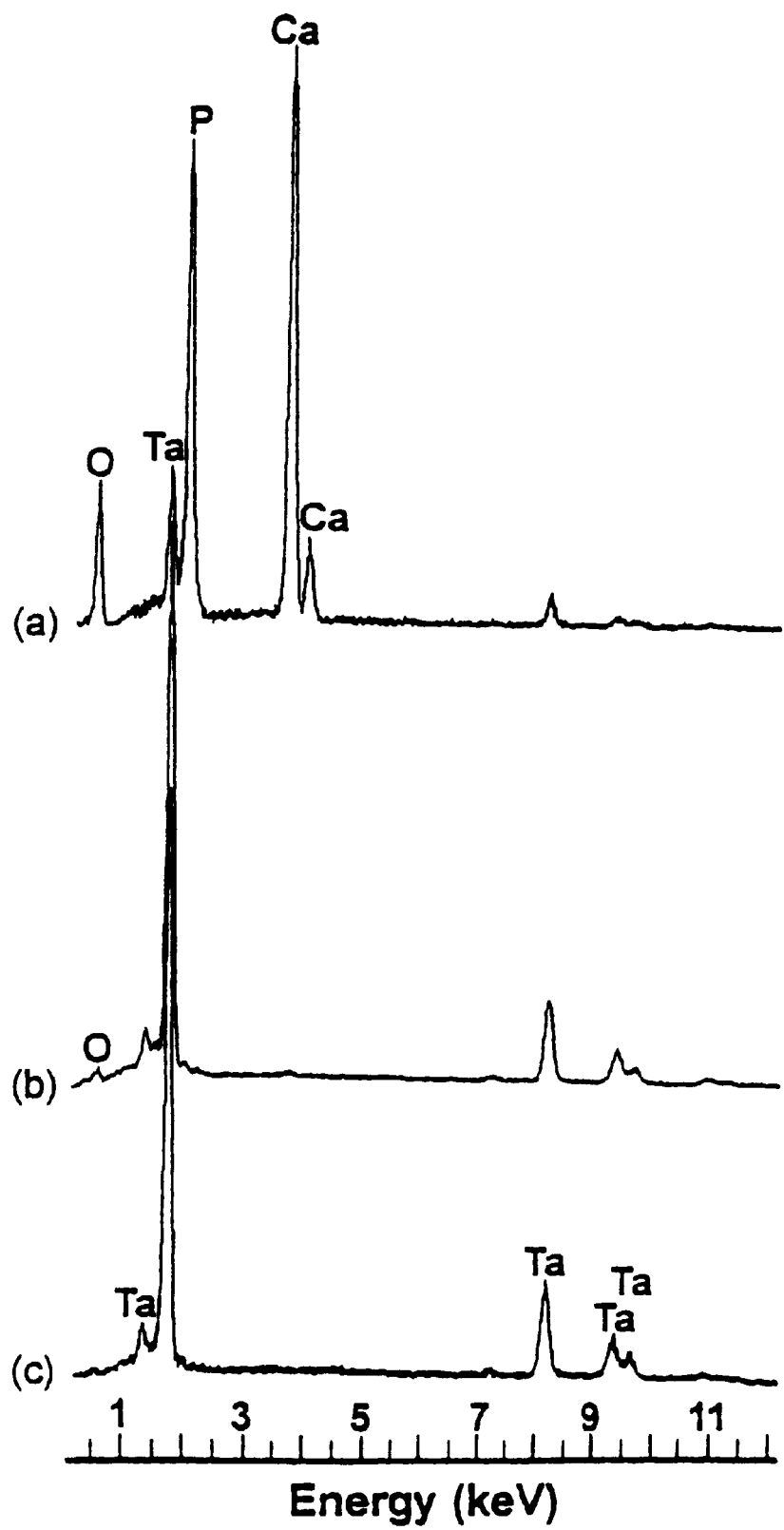
FIG. 15. EDX spectra of (a) non-treated, (b) treated, and (c) Pre-Ca treated, 2 day, FCS immersed porous tantalum (Ta) sample.
Figure 16:
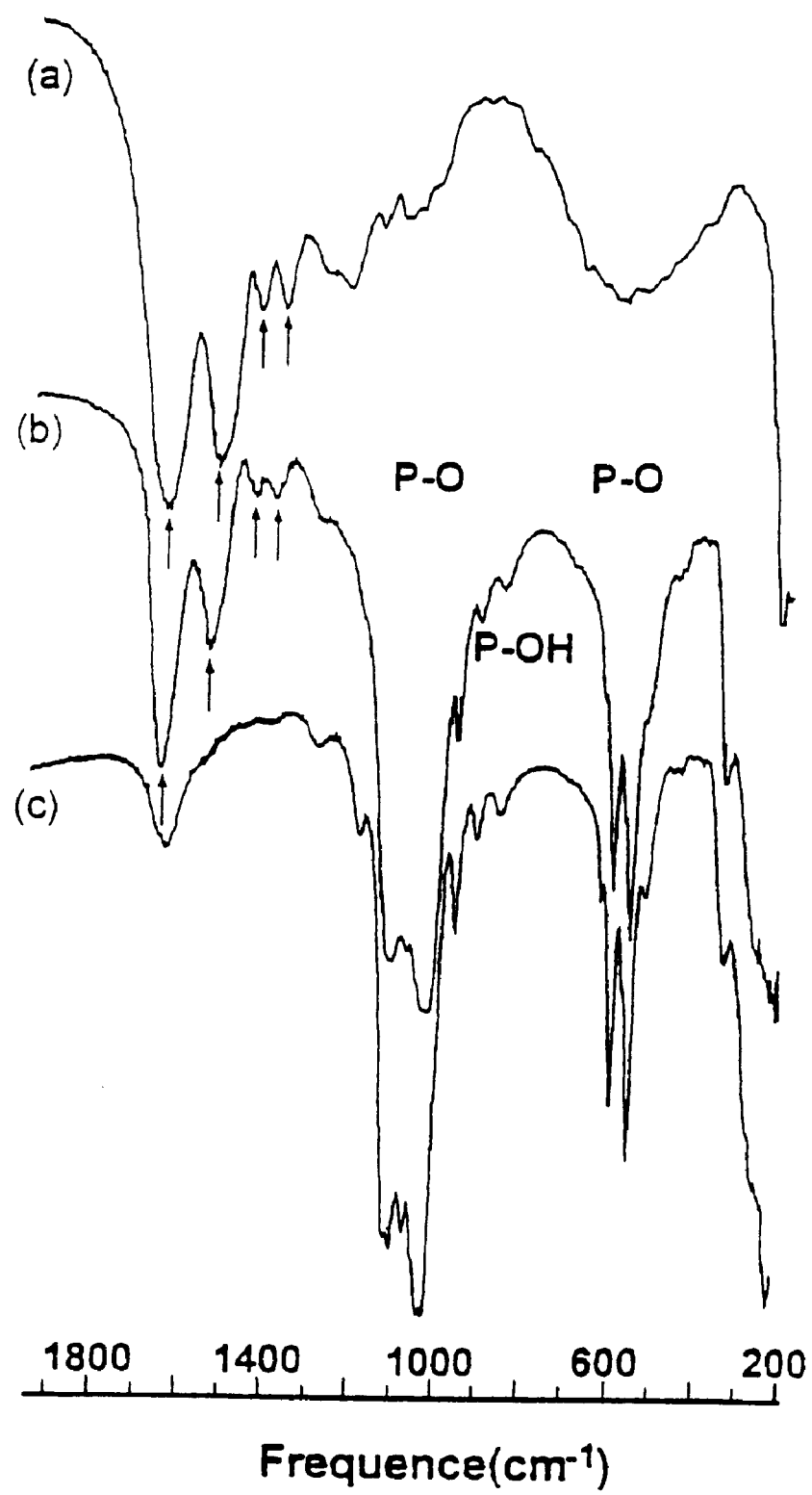
FIG. 16. IR spectra of BSA (a) and cp.Ti surfaces after 2 days of immersion in FCS containing 0.2% wt. BSA (b) and FCS only (c). The existence of four absorption bands of BSA in spectrum (b) indicates the co-precipitation of BSA with the biomimetic calcium phosphate coating.

FIG. 9 shows that a biomimetic Ca-P coating, approximately 16 $\mu$m thick, was formed on treated cp.Ti after 16 hours of immersion in FCS with Pre-Ca. The coating got thicker with immersion time as indicated by EDX (FIG. 10) and XRD (FIG. 11) results. The precipitation rate of the Ca-P coating in HBSS is slower than that in FCS. But the coating from HBSS (FIG. 12) was much denser than that from FCS. The coating from HBSS mainly consisted of apatite (FIG. 13). Biomimetic Ca-P coatings could also be precipitated on porous Ta samples (FIG. 14) after the treatment. The surface content change of the sample was detected by EDX as shown in FIG. 15. It is noteworthy that no precipitation was observed on any untreated samples after 2 weeks of immersion in FCS or HBSS, even with Pre-Ca. The formation of a specific titanium and tantalum oxide layer after their treatments is probably the main reason for the inductive precipitation of Ca-P coatings by means of in vitro immersion in SCS. The procedure of the treatments for titanium implants and tantalum could not be exchanged, otherwise no Ca-P coating was acquired. It is interesting to find that the results of co-precipitation of BSA and Ca-P coating were positive. The IR analyses (FIG. 16) indicated the obvious existence of BSA in the Ca-P coating on cp.Ti after immersion in FCS. Release experiments of BSA from BSA/Ca-P coatings are decribed in Example 4.

Conclusions

The results of this biomimetic calcium phosphate coating and protein co-precipitation study have shown that:—

The newly developed two-step chemical treatment is an effective method to prepare bioactive metallic implant surfaces allowing fast precipitation of adherent biomimetic Ca-P coatings by in vitro immersion in SCS. The chemical reagents needed for the treatment of titanium implant materials and tantalum are different from each other.

The precipitation of Ca-P coatings could be dramatically accelerated by means of pre-calcifying the treated samples before the immersions.

The precipitation rate and composition of the Ca-P coatings can be adjusted by controlling the components of the SCSs (FCS or HBSS) for immersion.

Some proteins like BSA can be co-precipitated with biomimetic Ca-P coatings. Such composite coatings, with other—bioactive-adsorbed organic molecules, are expected to be able to serve as potential drug-release systems.

EXAMPLE 4

Release of Bovine Serum Albumin (BSA) from calcium phosphate (Ca-P)/BSA coatings on surface-treated commercially pure titanium Co-precipitation of BSA Commercially rectangular blocks in size 10×10×2 mm were used as substrates. The two-step treatment and pre-calcification were performed on the metals as described in example 3. The supersaturated calcification solution used for immersion was prepared by dissolving 0.2% BSA into 0.8 ACS. All the samples were immersed in a 37° C. water-bath for two days.

Release experiments

The BSA content in solution was measured by means of the total organic carbon (TOC) method. Four blocks with Ca-P/BSA coatings were completely dissolved by 40 ml of 0.5 N HCl solution to detect the concentration of BSA in Ca-P/BSA coating. Four samples were immersed in 20 ml of 0.01 M PBS at pH 4 (adjusted using HCl) at 37° C. At certain intervals of time, 5 ml of the immersion solution was taken for TOC measurement at certain interval and then refilled to 20 ml with new PBS at pH 4 every time.

Results

BSA concentration in Ca-P/BSA coating

The Ca-P/BSA coatings on five samples were peeled off completely and then weighed using a balance. The weight of the Ca-P/BSA coating on each sample can be estimated to be a mean of 1.5 mg. The carbon concentration in the coating was calculated to be 15% and the BSA concentration was about 30% because the carbon concentration in BSA was detected to be around 50% by the same method.

BSA Release curve

Figure 17:
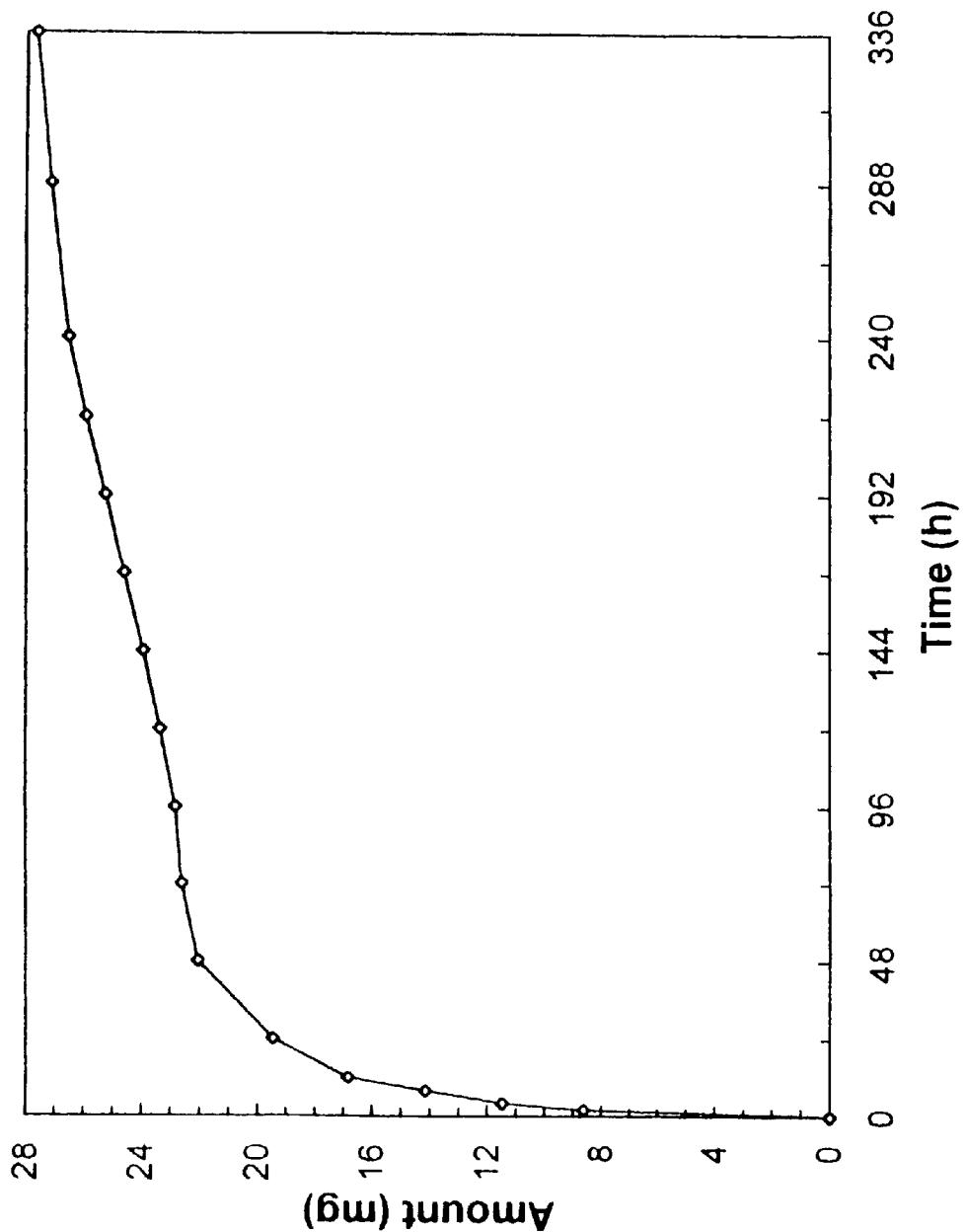
FIG. 17. The amount of BSA released into PBS as a result of the immersion time.

The amount of BSA released into PBS was plotted against the immersion time as shown in FIG. 17. It is indicated that under these experimental conditions, BSA was released relatively fast in the first two days of the immersion and then the release rate levelled off somewhat. The main reason could be that the PBS was very acidic (pH=4) at the beginning stage and the coating was dissolved very fast. After certain time of immersion the pH became higher. The pH values of PBS at the 7th and 14th were measured to be 5.628 and 5.584, respectively. Relating these results to the actual in vivo situation, where the pH value will be around 7, these results indicate that a gradual, slow release system is obtained, assuming that the 48 hour incubation in an acidic medium is comparable to several weeks, if not months implantation in an organism.

Conclusion

This experiment shows that proteins such as BSA can be co-precipitated in a calcium phosphate coating and can subsequently be released from the coating. Although BSA was used to examine the feasibility of this technique, it is clear that a Ca-P/biologically active agent composite coating can be used as sort of a drug delivery system and has therefore potential in the medical field.

TABLE 1

Surface roughness measurements results

| Surface finish | $R_a$ ($\mu$m) | $R_z$ ($\mu$m) | $R_{max}$ ($\mu$m) |
| --- | --- | --- | --- |
| Ti—6Al—4V 1200 grit | 0.47 ± 0.01 | 3.74 ± 0.04 | 5.13 ± 0.08 |
| Ti—6Al—4V 4000 grit | 0.24 ± 0.03 | 1.91 ± 0.31 | 2.46 ± 0.54 |
| Ti—6Al—4V 1 $\mu$m | 0.03 ± 0.00 | 0.35 ± 0.05 | 0.48 ± 0.03 |
| Ti—Al—2.5Fe 1200 grit | 0.42 ± 0.03 | 2.97 ± 0.35 | 3.47 ± 0.48 |
| Ti—Al—2.5Fe 4000 grit | 0.23 ± 0.01 | 1.97 ± 0.18 | 2.46 ± 0.34 |
| Ti—Al—2.5Fe 1 $\mu$m | 0.04 ± 0.01 | 0.28 ± 0.11 | 0.36 ± 0.19 |
| 316 L 1200 grit | 0.3 ± 0.06 | 2.32 ± 0.47 | 2.96 ± 0.03 |
| 316 L 4000 grit | 0.04 ± 0.01 | 0.35 ± 0.1 | 0.46 ± 0.1 |

TABLE 2

List of $Ca^{2+}$ and $HPO_4^{2-}$ concentrations, precipitation rate and composition of Ca—P coatings on cp.Ti and Ti6Al4V.

|  |  | FCS | HBSS |
|---|---|---|---|
| Concentration (mM) | $Ca^{2+}$ | 3.0 | 1.26 |
|  | $HPO_4^{2-}$ | 1.87 | 0.78 |
| Precipitation rate of coating | No Pre-Ca | 0.5 µm/hr | 1 µm/wk |
|  | Pre-Ca | 1 µm/hr | 3 µm/wk |
| Composition of coating |  | apatite, OCP | apatite |

Literature references

1. Y. Fujishiro, T. Sato and A. Okuwaki, "Coating of hydroxyapatite on metal plates using thermal dissociation of calcium -EDTA chelate in phosphate solutions under hydrothermal conditions", *J. Mater. Sc: Mater in Med,* 6, pp. 172–176, 1995
2. S. R. Radin and P. Ducheyne, *J. Biom. Mater. Res.,* 27, pp. 35, 1993
3. T. Hanawa, "Titanium and its oxide film: a substrate for forming apatite", in Proc. of the Bone Biomaterial Interface Workshop, Toronto, Dec. 1990, J. E. Davies ed., Univ. Toronto Press, pp. 49–61, 1991
4. Li, P, PhD. thesis Leiden University (1993)
5. P. Ducheyne, S. Radin and K. Ishikawa, "The rate of calcium phosphate precipitation on metal and ceramics, and the relationship to bioactivity", in Bone Bonding Biomaterials, P. Ducheyne, T. Kokubo & C. A. van Blitterswijk (eds), Reed Heathcare Communications, pp. 213–218, 1992.

What is claimed is:

1. An implantable device comprising a material having a precipitate enhancing roughened surface, before coating with an average peak distance between 10 nm and 1,000 nm and having an average depth, wherein the roughened surface is coated in vitro with a layer of a precipitate comprising calcium ions, phosphate ions, and an organic biologically active agent wherein at least a portion of the layer has a thickness greater than the average depth of the roughened surface.

2. The implantable device according to claim 1, wherein the organic biologically active agent is selected from the group consisting of growth factors, lipids, (lipo) polysaccharides, cytostatic agents, hormones, antibiotics, proteins, and mixtures thereof.

3. The implantable device according to claim 1, wherein the roughened surface, before coating, has an average depth between about 20 nm and about 2,000 nm.

4. The implantable device according to claim 1, wherein the layer has a thickness of about 50 nm to about 200 µm.

5. The implantable device according to claim 1, wherein the material is selected from the group consisting of a metal, a metal alloy, a ceramic material, a natural or synthetic polymer and a composite thereof.

6. A method of implanting a member selected from the group consisting of a bone substitute, a joint prosthesis, a dental implant, a maxillofacial implant, a vertebral surgery aid, and a transcutaneous device, comprising implanting a device according to claim 1.

7. The implantable device according to claim 1 wherein the layer is an amorphous crystalline layer.

8. The implantable device according to claim 1 wherein the layer comprises calcium ions and phosphate ions and one or more ions selected from the group consisting of hydroxide, chloride, sulphate, and nitrate anions and hydrogen, sodium, potassium and magnesium cations.

9. The implantable device according to claim 1 wherein the layer does not comprise hydroxyapatite.

10. The implantable device according to claim 5 wherein the metal is titanium or tantalum and the metal alloy is a titanium alloy.

* * * * *